United States Patent [19]
Forgacs et al.

[11] Patent Number: 5,793,490
[45] Date of Patent: Aug. 11, 1998

[54] METHOD AND AN APPARATUS FOR DETECTING CONCENTRATIONS OF FIRST AND SECOND TONER PARTICLES IN A DISPERSION

[75] Inventors: Peter Forgacs, Kiryat Gat, Israel; Benzion Landa, Edmonton, Canada

[73] Assignee: Indigo N.V., Maastricht, Netherlands

[21] Appl. No.: 360,687

[22] PCT Filed: Jul. 2, 1992

[86] PCT No.: PCT/NL92/00118

§ 371 Date: Mar. 2, 1995

§ 102(e) Date: Mar. 2, 1995

[87] PCT Pub. No.: WO94/01756

PCT Pub. Date: Jan. 20, 1994

[51] Int. Cl.$^6$ ................. G01J 4/00; G01N 21/59
[52] U.S. Cl. ................. 356/364; 356/436; 356/442
[58] Field of Search ................. 356/364–367, 356/432–436, 441–442, 411, 410, 445–446; 250/225, 574; 355/246; 118/691

[56] References Cited

U.S. PATENT DOCUMENTS

| | | |
|---|---|---|
| 3,283,644 | 11/1966 | Saltzman. |
| 3,518,003 | 6/1970 | Meyn. |
| 3,724,957 | 4/1973 | Tamate et al. ............... 356/367 |
| 4,166,702 | 9/1979 | Okamoto et al. |
| 4,171,916 | 10/1979 | Simms et al. ............... 356/366 |
| 4,579,253 | 4/1986 | Shenier. |
| 4,660,152 | 4/1987 | Downing et al. ............... 364/509 |
| 5,570,193 | 10/1996 | Landa et al. ............... 356/440 |

FOREIGN PATENT DOCUMENTS

| | | |
|---|---|---|
| 1598925 | 10/1971 | Germany. |
| 1148943 | 6/1989 | Japan. |

OTHER PUBLICATIONS

International Search Report and Annex.

*Primary Examiner*—Hoa Q. Pham
*Attorney, Agent, or Firm*—Greenblum & Bernstein P.L.C.

[57] ABSTRACT

Concentration detection of first and second toner particles in a dispersion, including illuminating the dispersion with linearly polarized light having a given polarization direction, detecting an amount of light passed through the dispersion and through an analyzer set at a predetermined angle to the given polarization direction and determining at least the concentration of one of the toner particles utilizing the detected amount of light. Additionally the concentration detection may include further illuminating the dispersion with unpolarized light, and further detecting a second amount of light passed through the dispersion illuminated with the unpolarized light, where both of the toner particle concentrations are determined from the detected and the second detected amounts of light.

22 Claims, 7 Drawing Sheets

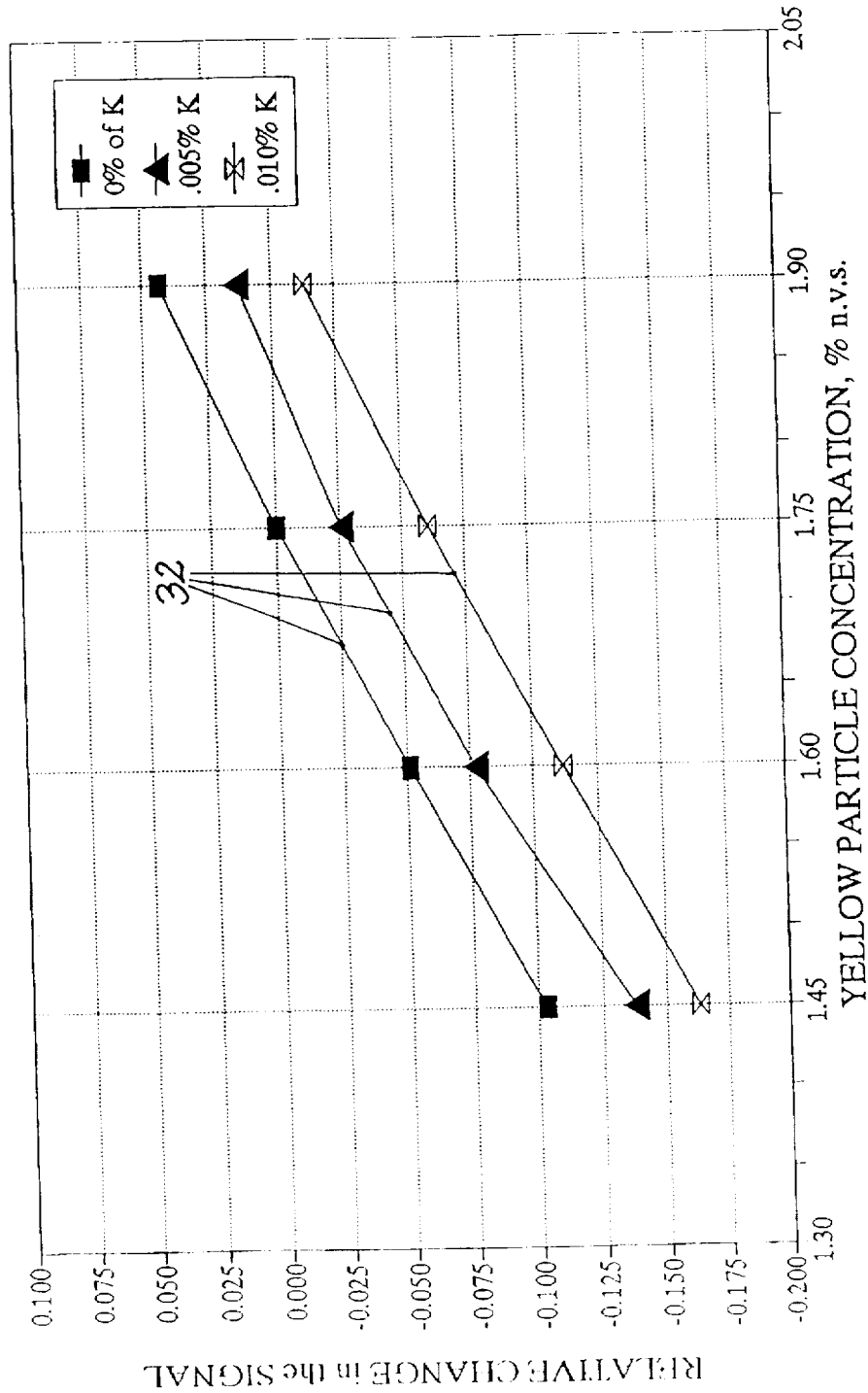

METHOD AND AN APPARATUS FOR DETECTING CONCENTRATIONS OF FIRST AND SECOND TONER PARTICLES IN A DISPERSION

FIELD OF THE INVENTION

The present invention relates to the field of concentration detection and more particularly to the detection of toner concentration in color liquid developer compositions especially in the presence of contaminants.

BACKGROUND OF THE INVENTION

In liquid developer systems the liquid developer is generally comprised of a carrier liquid and toner particles in a generally constant ratio. During imaging operations the concentration of toner particles is reduced and concentrated toner is added to return the concentration to its desired value.

It is important that the concentration of particles should be kept within a given range in order to realize consistent copy quality. This requirement is especially important in color printers or copiers, where the quality of the images is especially dependent on the color balance and on its stability.

In general, concentration of toner particles in liquid developers is determined by measuring the attenuation of light passing through a given path filled with the liquid developer. Since the particles absorb and scatter light, the attenuation of the light is related to the concentration of the particles.

U.S. Pat. No. 4,579,253 describes a system in which the beam of light is split into two components only one of which is attenuated by the liquid developer. The concentration is determined from the ratio of the attenuated and unattenuated beams.

Such systems work fairly well in single color systems or in multicolor systems in which there is no cross contamination between the colors. In general, the most troublesome cross-contamination is black toner particles in a relatively low attenuation color such as yellow. Since black has an attenuation several times that of yellow, visually negligible black contamination can effect the determination of the color concentration in a way which seriously disturbs the color balance of the system.

Japanese Patent Publication Kokai 1-148943 describes a system in which the attenuation of beams of light having two different colors are sequentially measured. Using these attenuation values, the publication describes a method for determining the concentration of both the black and the color particles.

SUMMARY OF THE INVENTION

The present invention is based on an analysis of the different factors which are operative in the attenuation of light by toner particles.

The two main factors are the absorption of light and the scatter of light by the particles. In general, for black toner particles, the effect of scatter is very small compared to the effect of absorption. On the other hand, for colored toner particles, especially for yellow, the effect of scatter is much greater than that of absorption.

One preferred embodiment of the present invention utilizes measurements which are selectively more sensitive to one of these effects thereby reducing the influence of the contaminant on the measurement of the color toner.

In a second, particularly preferred, embodiment of the invention, two measurements are made, one of which is relatively more sensitive to absorption and the other of which is relatively more sensitive to scatter. From these measurements and a knowledge of the scatter and absorption characteristics of the different particles, the concentration of both types of particles can be determined. Alternatively, a prioi knowledge of the attenuation of different concentration combinations to the two measurements can be used and direct knowledge of the scatter and absorption characteristics of the particles is not necessary.

In this second embodiment, a first measurement is made using polarized light to illuminate a cell containing liquid developer. A cross-polarizer (analyzer) is placed before a light detector on the other side of the cell. In the absence of scatter, no light would be detected at the detector. On the other hand, scatter also depolarizes the light and in the presence of scatter, light will be detected at the detector. In a second measurement, initially unpolarized light is used to illuminate the cell. In this case, the light output will be decreased mainly by absorption.

Due to different strengths of the two attenuation mechanisms in different toner types, the two measurements can be used to separately determine the two concentrations.

There is therefore provided in a preferred embodiment of the invention a method for detecting concentrations of first, generally colored, and second, generally black, toner particles in a dispersion, the method comprising the steps of:

illuminating the dispersion with linearly polarized light having a given polarization direction;

detecting an amount of light passed through the dispersion and through an analyzer set at a predetermined angle to the given polarization direction; and determining at least the concentration of one of the toner particles utilizing the detected amount of light.

Preferably the method also includes the steps of:

further illuminating the dispersion with unpolarized light; and further detecting a second amount of light passed through the dispersion illuminated with the unpolarized light;

wherein the step of determining includes the step of determining both of the toner particle concentrations from the detected and the second detected amounts of light.

Preferably the predetermined angle is 90 degrees.

In a preferred embodiment of the invention the method includes as a preparatory step, the step of determining the sensitivities of the detected and second amounts of light to known concentrations of first and second toner particles.

Alternatively, in a preferred embodiment of the invention the predetermined angle is set such that the sensitivity of the detected amount of light to the concentration of one of the toner particles is substantially zero whereby variations in the detected amount of light are substantially dependent only on the concentration of the other of the toner particles.

BRIEF DESCRIPTION OF THE DRAWINGS

The invention will be better understood from the following detailed description of the preferred embodiments of the invention in conjunction with the following drawings in which:

FIGS. 2A and 2B are graphical illustrations of the relative change in a detector signal as a function of yellow solid content for unpolarized and polarized light, respectively;

DETAILED DESCRIPTION OF PREFERRED EMBODIMENTS

Figure 1:
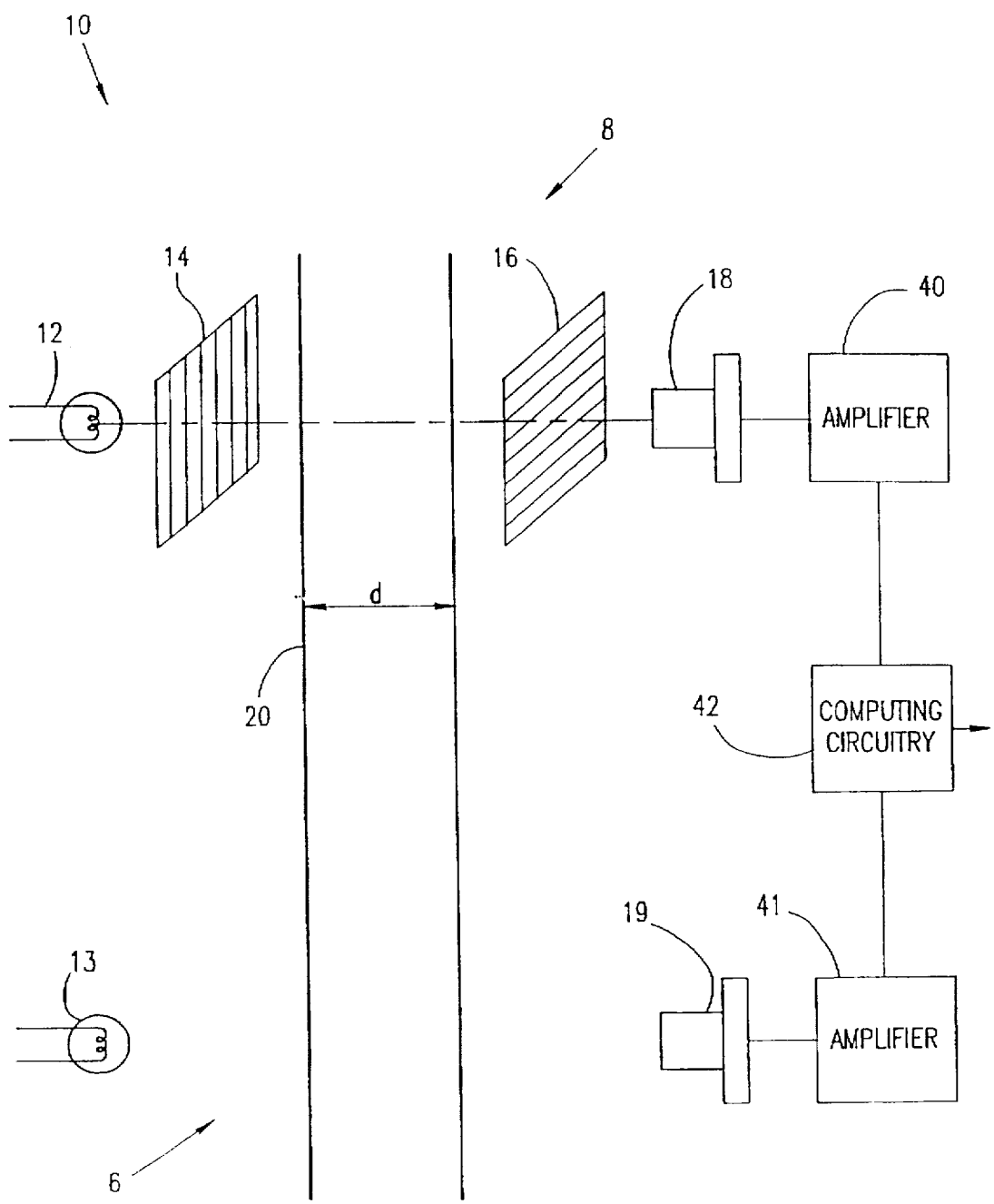
FIG. 1 is a schematic illustration of a concentration detector utilizing polarized light, constructed and operative in accordance with an embodiment of the present invention.
Figure 2A:
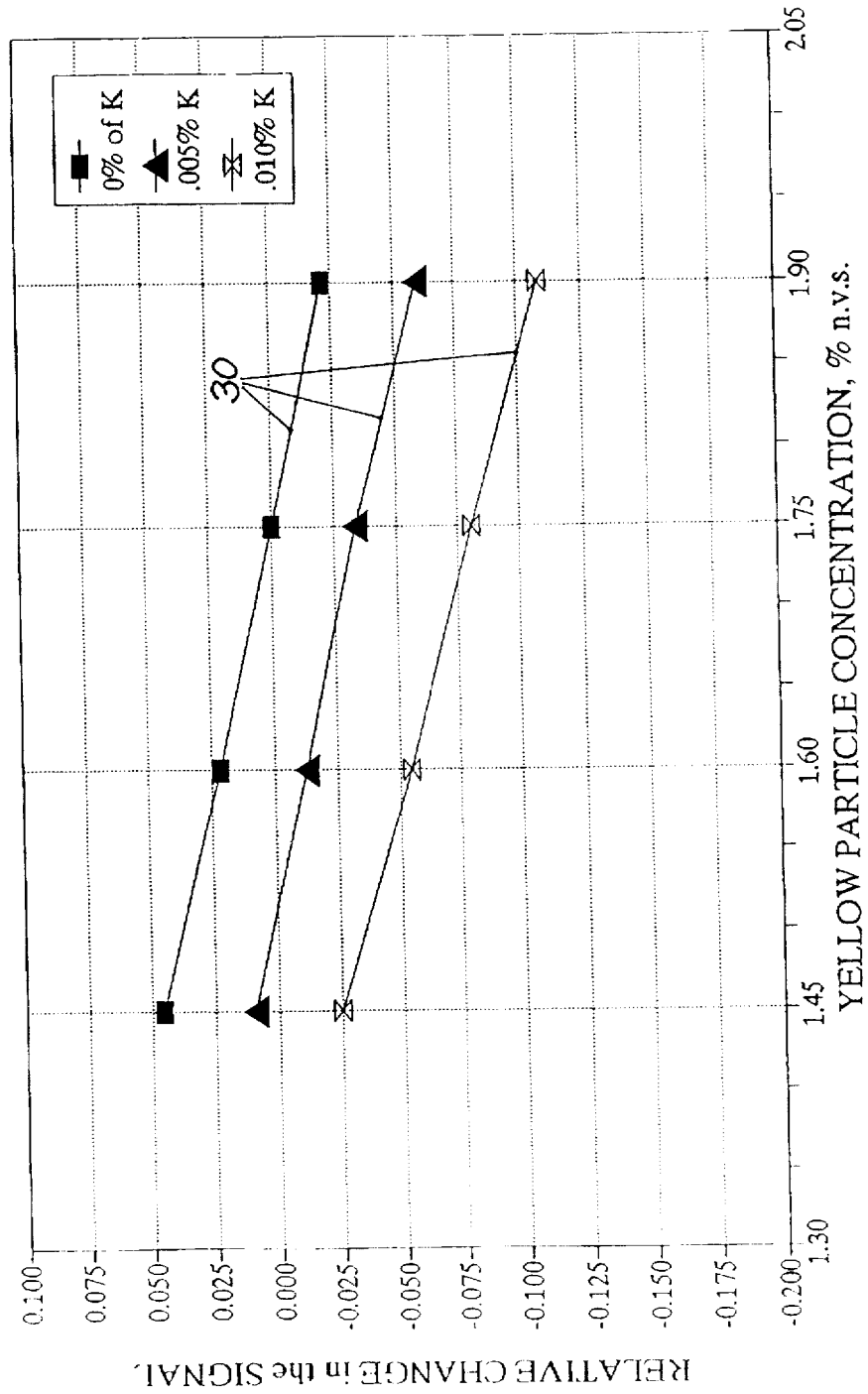
Figure 3A:
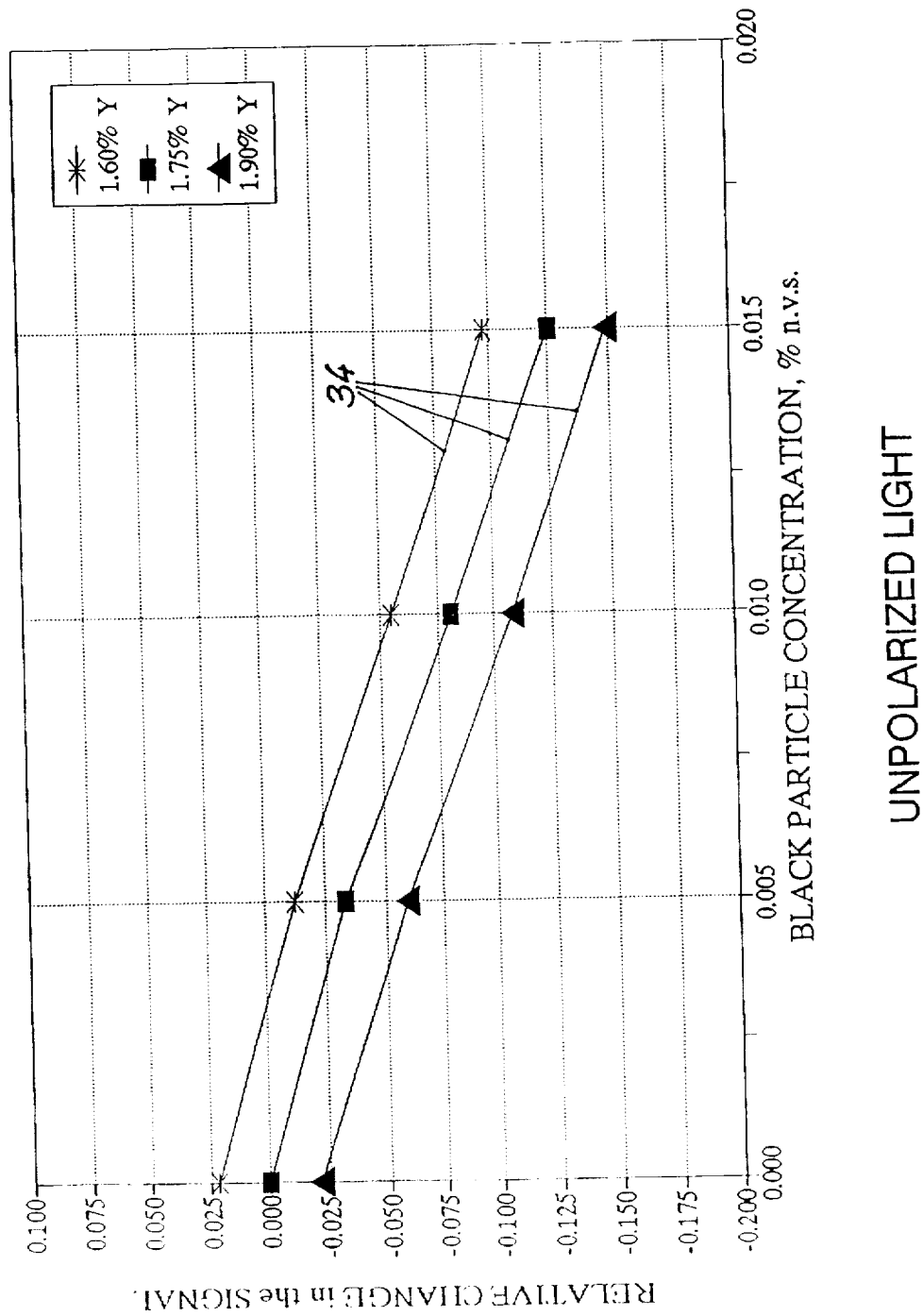
FIGS. 3A and 3B are graphical illustrations of the relative change in a detector signal as a function of black solid content for unpolarized and polarized light, respectively.
Figure 3B:
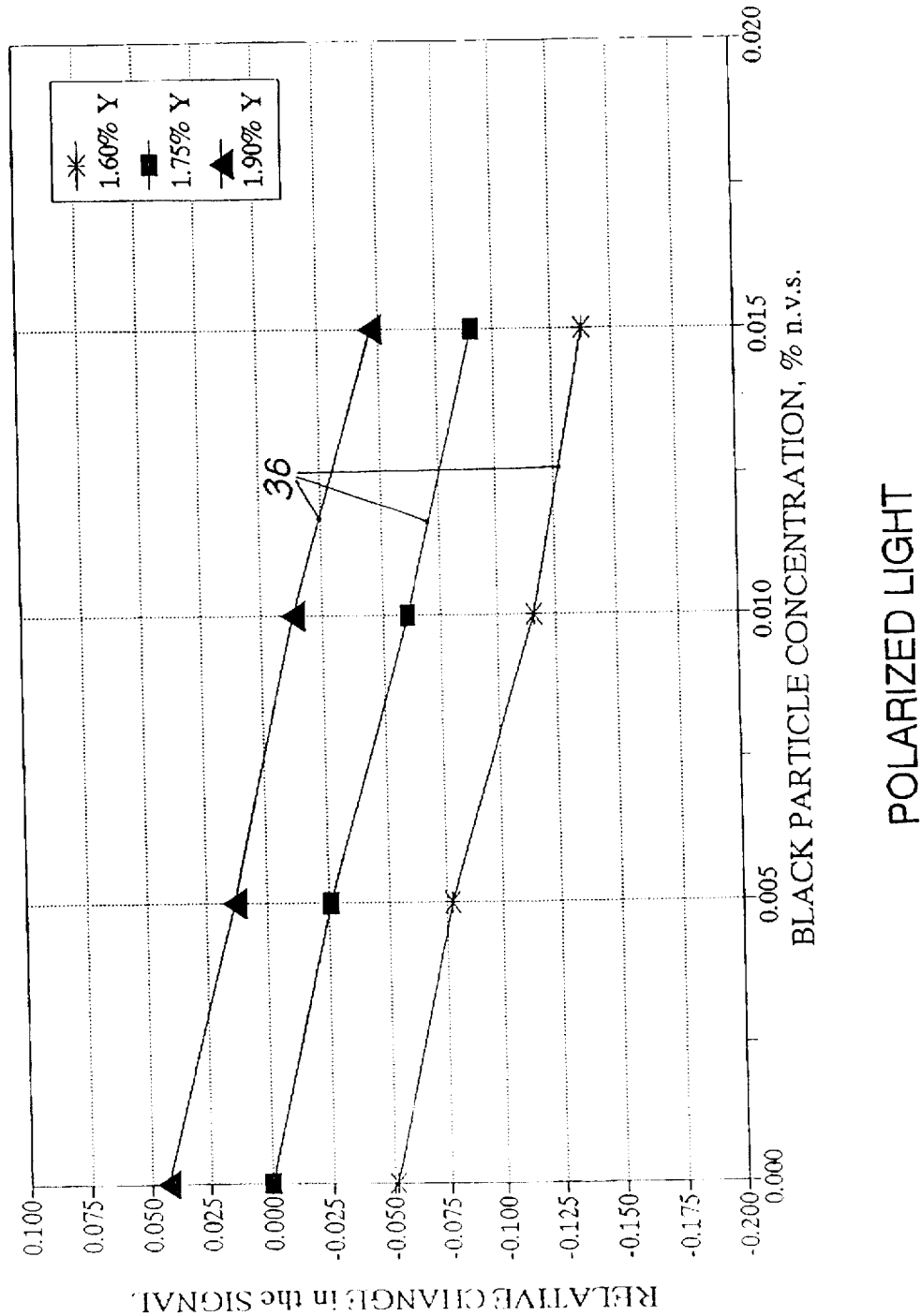

Reference is now made to FIGS. 1, 2A, 2B, 3A and 3B. FIG. 1 illustrates a concentration detector 10 constructed and operative in accordance with a preferred embodiment of the present invention. FIGS. 2A and 3A illustrate detected light strength using a first portion 6 of concentration detector 10 and FIGS. 2B and 3B illustrate detected light strength using a second portion 8 of concentration detector 10. First portion 6 corresponds generally to simple prior art concentration detectors.

The concentration detector 10 typically comprises two light sources 12 and 13, a polarizer 14 for linearly polarizing the light from light source 12, an analyzer 16 crossed to the polarizer 14 and two light detectors 18 and 19, such as photoresistors or photodiodes. A dispersion 20 is placed between the light detector 19 and light source 13 as well as between polarizer 14 and analyzer 16. Light detector 19 detects the light passed through dispersion 20 light detector 18 detects the light additionally passed through analyzer 16.

Dispersion 20 can be developer liquid containing colored toner particles. Preferably, dispersion 20 comprises only one type of colored particle; however, in practice, the dispersion may be contaminated by small amounts of particles of another color.

Some of the particles in dispersion 20 scatter and depolarize the polarized light transmitted through polarizer 14. Due to the presence of analyzer 16, placed at a predetermined angle, of typically 90 degrees, to the direction of the initially polarized light, detector 18 detects components of light which is at the predetermined angle.

Black particles strongly absorb incident light whereas colored particles, such as yellow particles, absorb very little incident light. Colored particles, on the other hand, scatter incident light.

Thus, in accordance with the present invention, concentration detector 10 can differentiate the types of particles, as can be seen with the aid of FIGS. 2A, 2B, 3A and 3B. FIGS. 2A and 2B illustrate the relative change in the detector signal as a function of varying yellow particle concentration and fixed black particle concentration. While the curves are based on illumination with white light, preferably, light having the same color as the particles is used. Concentration is given as a percentage of non-volatile toner solids (n.v.s.) in the liquid dispersion. Three curves are presented, one each for three different concentrations of black, as noted in the legend. FIG. 2A provides, as curves 30, output from light detector 19 (i.e., from first portion 6) and FIG. 2B provides, as curves 32, output from light detector 18 (i.e., from second portion 8).

It is noted that curves 30 have negative slopes, that curves 32 have positive slopes and that curves 30 and curves 32 are generally parallel to each other.

The information of FIGS. 2A and 2B is presented in FIGS. 3A and 3B, respectively, as functions of black particle concentration for a fixed concentration of yellow particles. It is noted that the curves, labeled 34 and 36, respectively, have negative slopes.

As can be seen from FIGS. 2A, 2B, 3A and 3B, black toner particles which contaminate the colored developer liquid result in a reduction of output for both polarized and unpolarized measurements (i.e. output of light detectors 18 and 19, respectively) while an increase in colored toner particle concentration increases the output for the polarized case and decreases the output for the unpolarized case. Furthermore, since curves 30-36 are substantially parallel straight lines, the effects of color imbalance and black cross-contamination are seen to be substantially independent. Under these circumstances, the concentrations of black and colored toner particles can be determined from two measurements, namely, the deviation of the output for polarized and unpolarized measurements, $\delta I_p$ and $\delta I_u$, respectively, from some predetermined, nominative, polarized and unpolarized measurements, by solving the matrix formula:

$$\begin{bmatrix} \delta I_p \\ \delta I_u \end{bmatrix} = \begin{bmatrix} del\_I_p/del\_C_y & del\_I_p/del\_C_b \\ del\_I_u/del\_C_y & del\_I_u/del\_C_b \end{bmatrix} \begin{bmatrix} \delta C_y \\ \delta C_b \end{bmatrix} \quad (1)$$

where $\delta C_y$ and $\delta C_b$ are the deviations of the current concentrations of the yellow and the black particles, respectively, from two nominative concentrations, such as 1.75% n.v.s. yellow and 0% n.v.s. black. The partial derivatives $del\_I_p/del\_C_y$, $del\_I_p/del\_C_b$, $del\_I_u/del\_C_y$, and $del\_I_u/del\_C_b$ are the slopes of curves 32, 36, 30 and 34, respectively, in the vicinity of the nominal concentrations.

It is noted that, because the curves in each of FIGS. 2A, 2B, 3A and 3B are generally straight and parallel, the derivatives, to first order, do not depend on the concentration. Further since three of the curves have a negative slope and one has a positive slope the determinant of the partial derivative matrix is not zero. Furthermore, as indicated hereinabove, curves 30-36 are generally linear which indicates that the first order model of formula 1 is appropriate. Thus, formula 1 is appropriate and can be solved to yield two equations for the yellow and black deviations from nominal:

$$\delta C_y = \alpha \cdot (\delta I_p) + \sigma \cdot (\delta I_u) \quad (2)$$

$$\delta C_b = \beta \cdot (\delta I_p) + \phi \cdot (\delta I_u) \quad (3)$$

where:

$$\alpha = (del\_I_u/del C_b)/det \quad (4)$$

$$\beta = -(del\_I_u/del\_C_y)/det \quad (5)$$

$$\sigma = -(del\_I_p/del\_C_b)/det \quad (6)$$

$$\phi = (del\_I_p/del\_C_y)/det \quad (7)$$

where det is the determinant of the 2×2 matrix of formula (1).

The values in the determinant of (1) may be determined by selecting a standard concentration around which the concentrations of the black and colored toner will vary. A plurality of dispersions 20, having concentrations of black and colored toner at and in the vicinity of the standard concentration, are then prepared and the responses of detector 18 in the presence of polarized and unpolarized light for each dispersion 20 are noted. From these responses, the slopes of curves 30–36 are calculated and stored. The output of light detectors 18 and 19 for the nominative concentrations are also stored.

The determination of the deviations of concentration from nominal for either toner type thus requires finding $\alpha$, $\beta$, $\sigma$ and $\phi$ from the slopes using formulas 4–7 and then computing the deviations in the concentrations according to formulas 2 and 3. The values of $\alpha$, $\beta$, $\sigma$ and $\phi$ can be found once and stored in circuitry 42.

The output of detectors 18 and 19 is typically provided to amplifiers 40 and 41, respectively, which amplify the signals and provide the amplified signals to computing circuitry 42 which calculates, according to the above described procedure, the amount of contamination and which indicates when more toner particles are needed. Computing circuitry can include dedicated analog or digital circuitry, a digital or other memory, a computer such as a microprocessor or other apparatus which can determine the amounts of colored and contaminant toner particles.

It will be appreciated by those skilled in the art, that utilizing the polarizing films of polarizer 14 and analyzer 16 is less expensive than using colored filters and special lamps as is necessary for the prior art concentration detectors.

Figure 4A:
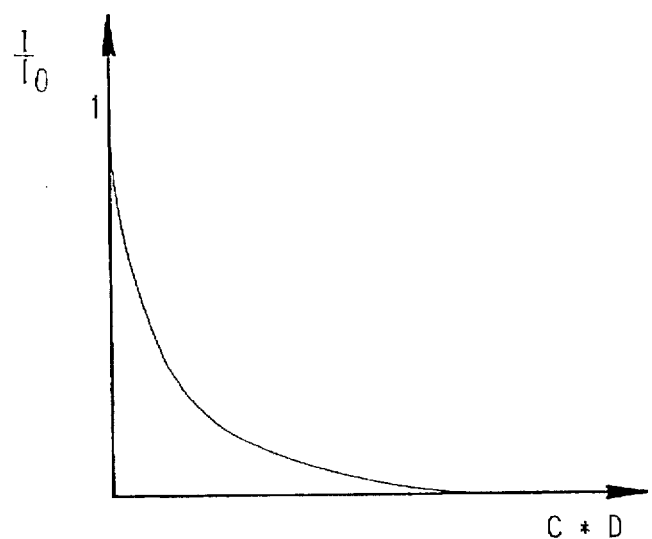
FIG. 4A is a graphical illustration of a model of the amount of incident light received at a detector in the presence of particles which attenuate light.
Figure 4B:
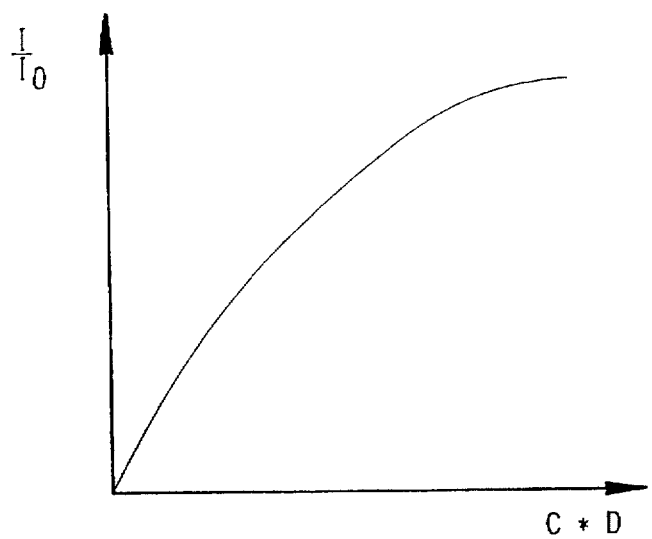
FIG. 4B is a graphical illustration of a model of the amount of incident light received at a detector in the presence of particles which scatter and depolarize light.
Figure 4C:
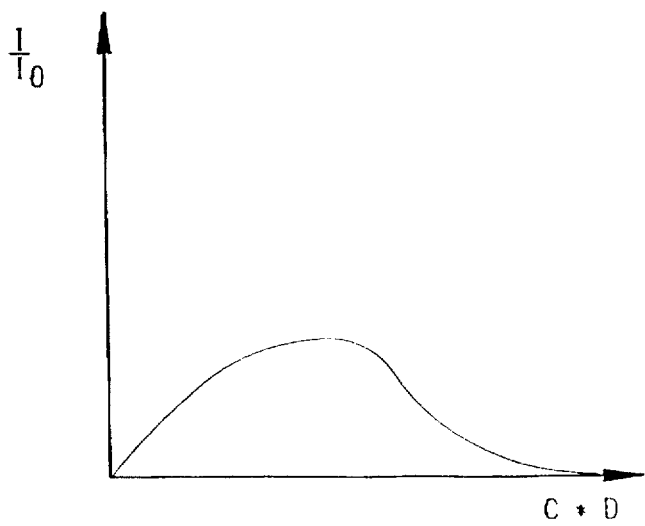
FIG. 4C is a graphical illustration of a model of the amount of incident light received at a detector in the presence of particles which attenuate and scatter light.

Reference is now briefly made to FIGS. 4A–4C which provide models of the response of the light detectors in the presence of particles which attenuate, depolarize and both attenuate and depolarize, respectively, as a function of the product of the concentration, C, and the length, d, of the light path in dispersion 20.

FIG. 4A indicates that a large portion of the unpolarized incident light $I_o$ is received as an intensity I by detector 19 (i.e. there is little attenuation) in dispersions with low particle concentrations and small thicknesses but that the portion received decreases exponentially as concentration and thickness increase.

FIG. 4B indicates that little polarized incident light $I_o$ is received by detector 18 (i.e. there is little depolarization) for dispersions with low particle concentrations and small thicknesses but that the amount of polarized incident light increases as concentration and thickness increase and levels off as the depolarization becomes complete.

FIG. 4C, which is a multiplication of the two curves of FIGS. 4A and 4B, indicates that, in the presence of particles which both attenuate and depolarize, the amount of incident light received by the detector first increases, reaches a peak and then decreases, as concentration and thickness increase.

It is noted that the effect of depolarization is strongest for low concentrations and/or small thicknesses d. Therefore, to ensure optimal operation of the concentration detector 10, the thickness d should be as small as possible.

It will be appreciated by those skilled in the art that, because black toner particles attenuate the light with very little depolarization, in order to maximally separate the two effects of depolarization and attenuation, light which causes the colored toner particles to maximally scatter and to minimally attenuate should be utilized. Therefore, ideally, light close to or the color of the colored toner particles should be utilized. For example, for measuring the concentration of yellow particles, yellow or red light should be used.

This is in contrast to the prior art which utilizes light of complementary colors. In the prior art, blue light is utilized to measure the attenuation in yellow liquid developer caused by black toner particles, which is the most troublesome cross-contamination. However, strong blue light is especially difficult to produce. Using light of the same or close to the color of the toner particles, as in the present invention, is advantageous in that dependence on the color of the light is much smaller than in the case of prior art use of complimentary colors where small deviations in color of the toner drastically changes the sensitivity of the sensor.

However, it is noted that the present invention is operative and more sensitive than the prior art with white light, as can be seen by the fact that the slopes of curves 32 are larger than those of curves 30. As discussed herein, an even more sensitive embodiment is the one with colored light of a color close to that of the colored toner.

Figure 5:
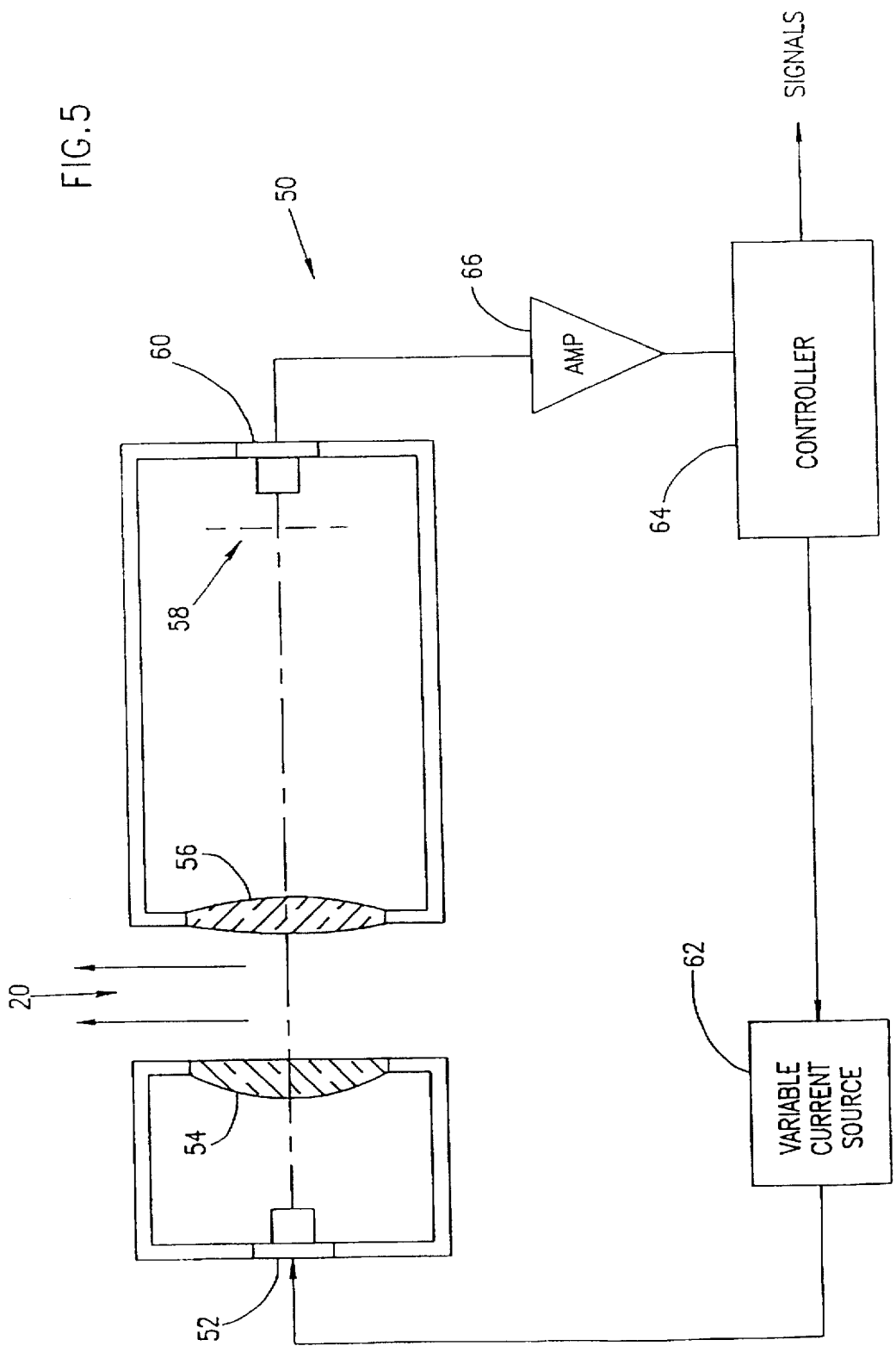
FIG. 5 is a schematic illustration of an alternative implementation of the concentration detector of FIG. 1.

Reference is now additionally made to FIG. 5 which illustrates an alternative embodiment of the present invention. This alternative concentration detector, labeled 50, typically comprises a laser diode 52, two lenses 54 and 56 between which dispersion 20 flows, a single analyzer 58 and a detector 60.

Laser diode 52 is operative to provide polarized light in response to a high input current and to provide non-polarized light when the current is reduced. Therefore, a variable current source 62 and a controller 64 which controls it are included in concentration detector 50 to control the type of light which laser diode 52 produces. Typically, an amplifier 66 is also included to amplify the output of detector 60 for controller 64.

The light from laser diode 52 is preferably received by lens 54 which collimates it before it passes through dispersion 20. The light from dispersion 20 is preferably focused by lens 56 onto detector 60. Alternatively, the lenses can be deleted.

When laser diode 52 produces polarized light, concentration detector 50 operates in the polarized mode described hereinabove. Otherwise, it operates in the unpolarized mode.

In accordance with an alternative embodiment of the present invention, concentration detector 50 can be utilized to measure the concentration of black particles only. In this embodiment, analyzer 58 is placed at an angle less than 90 degrees to the direction of polarization of a polarized light source such as diode 52 or an other source of polarized light such as elements 12 and 14 of FIG. 1.

It can be shown that there exists an analyzer angle for which the system is insensitive to the yellow concentration.

When analyzer 16 is at the same angle (0 degrees) as polarizer 14, then the effect of attenuation and scatter both reduce the output, thereby resulting in the negative sloped curves 30 of FIG. 2A. When the analyzer 16 is at 90 degrees to the polarizer 14, then the output is the positively sloped curves 32 of FIG. 2B, for the colored toner particles.

If the angle of analyzer 16 is moved from 0 degrees to 90 degrees with respect to the polarizer 14, curves 30 will decrease in negative slope until they have a 0 slope and then increase in slope until they have the slopes of curves 32.

Therefore, there is some angle between 0 and 90 degrees at which analyzer 16 can be placed which will produce a 0 slope for curves 30. At this angle, the effect of attenuation "cancels" the effect of depolarization for the colored particles and the output of detector 18 does not change as a function of concentration of the colored particles.

At this, typically experimentally found, angle, the changes in output measured by detector 18 are functions of the concentration of the black particles only.

Thus, in accordance with this embodiment of the present invention, the concentration of black contaminating particles can be directly measured after determining the sensitivity to the concentration of black toner particles.

In a further alternative embodiment of the present invention, polarized light alone, with the analyzer at 90 degrees to the direction of polarization, can be utilized. As can be seen from FIGS. 2A and 2B, the slopes of curves 32 (with polarized light) are larger than those of curves 30 (with unpolarized light). Thus if a single measurement with polarized light is utilized to determine the color concentration, this measurement will be less sensitive to black concentration than the unpolarized measurement of the prior art.

It will be appreciated by persons skilled in the art that the present invention is not limited to what has been particularly shown and described hereinabove. Rather the scope of the present invention is defined only by the claims which follow:

We claim:

1. A method for detecting concentrations of at least one of black and colored toner particles in a dispersion of colored toner particles possibly contaminated by black toner particles, the method comprising:

illuminating the dispersion with linearly polarized light having a given polarization direction;

detecting a first amount of light passed through the dispersion and through an analyzer set at a predetermined angle to the given polarization direction;

illuminating the dispersion with unpolarized light;

detecting a second amount of light passed through the dispersion illuminated with the unpolarized light; and determining at least one of the black and colored toner particle concentrations from at least one of the detected first and second detected amounts of light.

2. A method according to claim 1 wherein the determining includes determining both the black and colored toner particle concentrations from the first detected and the second detected amounts of light.

3. A method according to claim 2 and including preparatorily determining the sensitivities of the detection of the first and second amounts of light to known concentrations of first and second toner particles.

4. A method according to claim 3 and wherein the determining includes calculating the deviations of the concentrations of the first and the second particles, from the known concentrations, $\delta C_1$ and $\delta C_2$ respectively, from the following matrix formula:

$$\begin{bmatrix} \delta I_p \\ \delta I_u \end{bmatrix} = \begin{bmatrix} del\_I_p/del\_C_1 & del\_I_p/del\_C_2 \\ del\_I_u/del\_C_1 & del\_I_u/del\_C_2 \end{bmatrix} \begin{bmatrix} \delta C_1 \\ \delta C_2 \end{bmatrix}$$

wherein $\delta I_p$ and $\delta I_u$ are the deviations of the detected first and detected second amounts of light from their values at the known concentrations and wherein del\_$I_p$/del\_$C_1$, del\_$I_p$/del\_$C_2$, del\_$I_u$/del\_$C_1$ and del\_$I_u$/del\_$C_2$ are the sensitivities of the detected first (del\_$I_p$) and detected second (del\_$I_u$) amounts of light with respect to changes in the concentrations of the first (del\_$C_1$) and second (del\_$C_2$) particles in the vicinity of the known concentrations.

5. A method according to claim 1 and wherein the predetermined angle is 90 degrees.

6. A method for detecting concentration of black toner particles in a dispersion of black and colored toner particles comprising:

illuminating the dispersion with linearly polarized light having a given polarization direction;

detecting an amount of light passed through the dispersion and through an analyzer set at a predetermined angle to the given polarization direction;

determining at least the concentration of black toner particles utilizing the detected amount of light, wherein the predetermined angle is set such that the sensitivity of detecting the colored toner particles is substantially zero whereby variations in the detected amount of light are substantially dependent only on the concentration of the black toner particles.

7. Apparatus for detecting concentrations of at least one of black and colored toner particles in a dispersion, the apparatus comprising:

a source of polarized light polarized in a given polarization direction;

a source of unpolarized light;

at least one light detector placed with the dispersion between the light detector and the source of polarized light;

a second light detector placed with the dispersion between the second light detector and the source of unpolarized light;

an analyzer placed between the dispersion and the at least one light detector and set at a predetermined angle to the given direction; and computing circuitry which receives an output from the at least one light detector and an output from the second light detector and determines both of the toner particle concentrations responsive to outputs of the at least one light detector and the second light detector.

8. Apparatus according to claim 7 and wherein the predetermined angle is 90 degrees.

9. Apparatus according to claim 7 and also comprising initialization means for determining the sensitivities of the at least one light detector and the second light detector to known concentrations of first and second toner particles.

10. Apparatus according to claim 9 and wherein the computing circuitry receives as inputs $I_p$ from the at least one light detector and $I_u$ from the second light detector and generates the deviations of the concentrations of the first and the second particles, from the known concentrations, $\delta C_1$ and $\delta C_2$ respectively, from the following matrix formula:

$$\begin{bmatrix} \delta I_p \\ \delta I_u \end{bmatrix} = \begin{bmatrix} del\_I_p/del\_C_1 & del\_I_p/del\_C_2 \\ del\_I_u/del\_C_1 & del\_I_u/del\_C_2 \end{bmatrix} \begin{bmatrix} \delta C_1 \\ \delta C_2 \end{bmatrix}$$

wherein $\delta I_p$ and $\delta I_u$ are the deviations of the at least one light detector output and the second light detector output from their values at the known concentrations and wherein del\_$I_p$/del\_$C_1$, del\_$I_p$/del\_$C_2$, del\_$I_u$/del\_$C_1$ and del\_$I_u$/del\_$C_2$ are the sensitivities of the outputs of the at least one detector (del\_$I_p$) and the second light detector (del\_$I_u$) with respect to changes in the concentrations of the first (del\_$C_1$) and second (del\_$C_2$) particles in the vicinity of the known concentrations.

11. Apparatus according to claim 7 and wherein the predetermined angle is set such that the sensitivity of the detected amount of light to the concentration of one of the toner particles is substantially zero whereby variations in the detected amount of light are substantially dependent only on the concentration of the other of the toner particles.

12. Apparatus according to claim 7 wherein the illumination has a color substantially the same as that of the colored toner particles.

13. Apparatus for detecting concentrations of first and second toner particles in a dispersion, the apparatus comprising:

a source of light which is polarized in a given polarization direction in a first mode and being unpolarized in a second mode;

a light detector placed with the dispersion between the light detector and the source of light;

an analyzer placed between the dispersion and the light detector and set at a predetermined angle to the given direction;

means for changing the mode of operation between the first and second modes; and computing circuitry operative for determining the concentration of at least one of the toner particles utilizing output from the light detector.

14. Apparatus according to claim 13 wherein the source of light is a laser diode which is operative to produce unpolarized light when energized at a low first current and to produce polarized light while it is energized at a second, higher, current.

15. A method for detecting concentrations of at least one of black and colored toner particles in a dispersion of colored toner particles possibly contaminated by black toner particles, the method comprising:

illuminating the dispersion with linearly polarized light having a given polarization direction;

detecting a first amount of light passed through the dispersion and through an analyzer set at a predetermined angle to the given polarization direction;

further illuminating the dispersion with unpolarized light;

detecting a second amount of light passed through the dispersion illuminated with the unpolarized light; and determining at least one of the black and colored toner particle concentrations from at least one of the detected first and second detected amounts of light, said determining not being affected by light not passing through the analyzer during the illuminating of the dispersion with the linearly polarized light.

16. Apparatus for detecting concentrations at least one of black and colored toner particles in a dispersion, the apparatus comprising:

a source of polarized light polarized in a given polarization direction;

at least one light detector placed with the dispersion between the light detector and the source of light;

an analyzer placed between the dispersion and the at least one light detector and set at a predetermined angle to the given direction; and computing circuitry which receives an output from the at least one light detector and which determines the concentration of at least one of the toner particles responsive to said detector output, wherein said determining is insensitive to any of the polarized light not passing through the analyzer during the illuminating of the dispersion.

17. Apparatus for detecting concentrations at least one of black and colored toner particles in a dispersion, the apparatus comprising:

a source of polarized light polarized in a given polarization direction;

at least one light detector placed with the dispersion between the light detector and the source of light;

an analyzer placed between the dispersion and the at least one light detector and set at a fixed angle other than ninety degrees to the given direction; and computing circuitry operative for determining the concentration of at least one of the toner particles utilizing output from the at least one light detector.

18. Apparatus according to claim 17 and wherein the fixed angle is set such that the sensitivity of the detected amount of light to the concentration of one of the toner particles is substantially zero whereby variations in the detected amount of light are substantially dependent only on the concentration of the other of the toner particles.

19. Apparatus for detecting concentrations at least one of black and colored toner particles in a dispersion, the apparatus comprising:

a source of polarized light polarized in a given polarization direction;

only one light detector placed with the dispersion between the light detector and the source of light;

an analyzer placed between the dispersion and light detector and set at a predetermined angle to the given direction; and computing circuitry operative for determining the concentration of at least one of the toner particles utilizing output from the light detector.

20. Apparatus for detecting the concentration of at least one of black and colored toner particles in a dispersion of both black and colored toner particles, the apparatus comprising:

a source of polarized light polarized in a given polarization direction;

at least one light detector placed with the dispersion between the light detector and the source of light;

an analyzer placed between the dispersion and the at least one light detector and set at a predetermined angle to the given direction; and computing circuitry which receives an output from the at least one light detector and which determines the concentration of at least one of the types of toner particles in the presence of the other type, responsive to said detector output, wherein said determining is insensitive to any of the polarized light not passing through the analyzer during the illuminating of the dispersion.

21. Apparatus for detecting the concentration at least one of black and colored toner particles in a dispersion of black and colored toner particles, the apparatus comprising:

a source of polarized light polarized in a given polarization direction;

at least one light detector placed with the dispersion between the light detector and the source of light;

an analyzer placed between the dispersion and the at least one light detector and set at a fixed angle other than 90 degrees to the given direction; and computing circuitry operative for determining the concentration of at least one of the types of toner particles, in the presence of the other type of particles utilizing output from the at least one light detector.

22. Apparatus for detecting concentrations of at least one of black and colored toner particles in a dispersion of both black and colored toner particles, the apparatus comprising:

a source of polarized light polarized in a given polarization direction;

only one light detector placed with the dispersion between the light detector and the source of light;

an analyzer placed between the dispersion and the one light detector and set at a predetermined angle to the given direction; and computing circuitry operative for determining the concentration of at least one of the types of toner particles in the presence of the other type utilizing the output of the one light detector.

* * * * *